(12) United States Patent
Kunz

(10) Patent No.: US 10,660,513 B2
(45) Date of Patent: May 26, 2020

(54) SUPPORT AND GUIDE DEVICE FOR AN ENDOSCOPIC INSTRUMENT

(76) Inventor: Reiner Kunz, Kleinmachnow (DE)

( * ) Notice: Subject to any disclaimer, the term of this patent is extended or adjusted under 35 U.S.C. 154(b) by 0 days.

(21) Appl. No.: 13/122,612

(22) PCT Filed: Oct. 1, 2009

(86) PCT No.: PCT/EP2009/062778
§ 371 (c)(1),
(2), (4) Date: May 17, 2011

(87) PCT Pub. No.: WO2010/040685
PCT Pub. Date: Apr. 15, 2010

(65) Prior Publication Data
US 2011/0237881 A1    Sep. 29, 2011

(30) Foreign Application Priority Data

Oct. 9, 2008 (DE) .................. 10 2008 051 111

(51) Int. Cl.
*A61B 1/313* (2006.01)
*A61B 1/00* (2006.01)

(52) U.S. Cl.
CPC ........ *A61B 1/3132* (2013.01); *A61B 1/00147* (2013.01)

(58) Field of Classification Search
CPC .......................... A61B 1/00147; A61B 1/0016
USPC .......................................... 600/102; 606/130
See application file for complete search history.

(56) References Cited

U.S. PATENT DOCUMENTS

| 4,608,977 | A | * | 9/1986 | Brown ........................... 606/130 |
| 5,060,632 | A | * | 10/1991 | Hibino et al. ................. 600/109 |
| 5,154,723 | A | * | 10/1992 | Kubota et al. ................ 606/130 |
| 5,159,446 | A | * | 10/1992 | Hibino et al. ................... 348/65 |
| 5,201,742 | A | * | 4/1993 | Hasson ........................... 606/130 |
| 5,300,033 | A | * | 4/1994 | Miller ...................... 604/167.03 |
| 5,423,832 | A | * | 6/1995 | Gildenberg .................... 606/130 |
| 5,749,362 | A | * | 5/1998 | Funda et al. .................. 600/407 |

(Continued)

FOREIGN PATENT DOCUMENTS

| DE | 9414957 | 11/1995 |
| DE | 19526223 | 2/1996 |

(Continued)

OTHER PUBLICATIONS

Japanese Office Action dated Jun. 25, 2013, corresponding to Japanese Patent Application No. 2011-530459.

*Primary Examiner* — Timothy J Neal
*Assistant Examiner* — Jae Woo
(74) *Attorney, Agent, or Firm* — Ladas & Parry LLP; Malcolm J. MacDonald

(57) ABSTRACT

A support and guide device for an endoscopic instrument includes a first guide device extending substantially in a plane and bordering a surface, a first carriage that can travel along the first guide device, a second guide device connected to the first carriage and extending in a plane perpendicular thereto, a second carriage that can travel along the second guide device, a holder for the endoscopic instrument which is connected to the carriage and rotatable about the longitudinal axis of the carriage and moveable in the axial direction, and drive units for the first and the second carriages and for the holder for the endoscopic instrument. A control system is associated with the drive units.

15 Claims, 3 Drawing Sheets

(56) References Cited

U.S. PATENT DOCUMENTS

Figure 1:
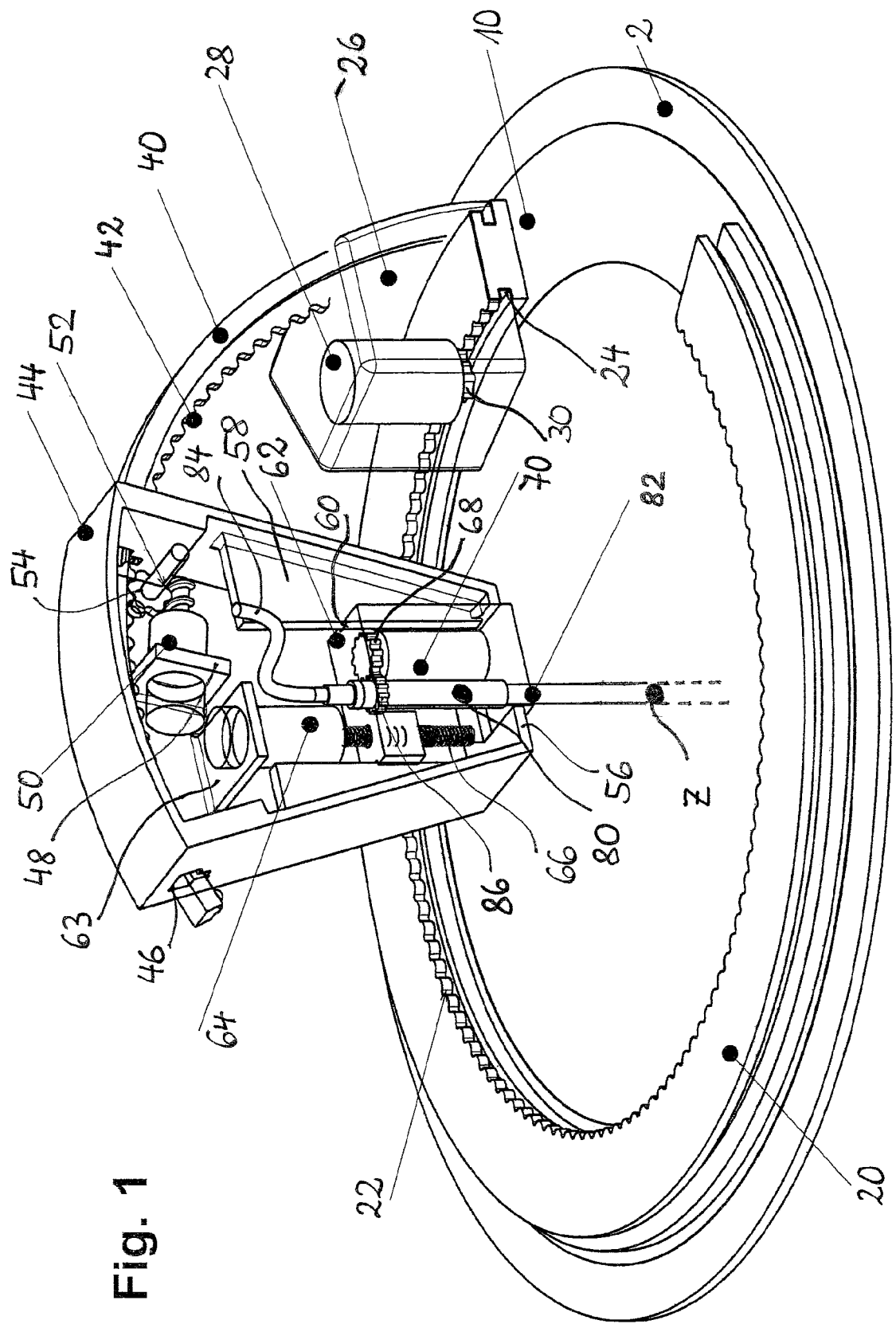

| | | | | |
|---|---|---|---|---|
| 5,891,158 | A * | 4/1999 | Manwaring et al. | 606/130 |
| 5,943,719 | A * | 8/1999 | Feldman et al. | 606/130 |
| 6,966,876 | B2 * | 11/2005 | Irion et al. | 600/102 |
| 6,989,015 | B2 * | 1/2006 | Daum et al. | 606/130 |
| 6,997,866 | B2 * | 2/2006 | Payandeh et al. | 600/102 |
| 7,022,066 | B2 * | 4/2006 | Yokoi et al. | 600/109 |
| 7,313,430 | B2 * | 12/2007 | Urquhart et al. | 600/429 |
| 7,636,596 | B2 * | 12/2009 | Solar | 600/429 |
| 9,549,719 | B2 * | 1/2017 | Shohat | A61B 17/3403 |
| 2003/0055436 | A1 * | 3/2003 | Daum et al. | 606/130 |
| 2003/0233110 | A1 * | 12/2003 | Jesseph | A61B 6/0414 |
| | | | | 606/167 |
| 2004/0049127 | A1 * | 3/2004 | Nezhat | A61B 17/3403 |
| | | | | 600/564 |
| 2005/0222582 | A1 * | 10/2005 | Wenchell | A61B 17/3423 |
| | | | | 606/108 |
| 2006/0100501 | A1 * | 5/2006 | Berkelman | A61B 17/3403 |
| | | | | 600/415 |
| 2006/0229641 | A1 * | 10/2006 | Gupta | A61B 17/3403 |
| | | | | 606/130 |
| 2006/0270902 | A1 * | 11/2006 | Igarashi et al. | 600/114 |
| 2007/0161855 | A1 | 7/2007 | Mikkaichi | |
| 2008/0058603 | A1 * | 3/2008 | Edelstein et al. | 600/201 |
| 2008/0167663 | A1 * | 7/2008 | De Mathelin et al. | 606/130 |
| 2008/0183191 | A1 * | 7/2008 | Schoepp | A61B 17/3403 |
| | | | | 606/130 |
| 2008/0269777 | A1 * | 10/2008 | Appenrodt et al. | 606/130 |
| 2008/0275466 | A1 * | 11/2008 | Skakoon | 606/130 |
| 2009/0171184 | A1 * | 7/2009 | Jenkins et al. | 600/411 |
| 2010/0010505 | A1 * | 1/2010 | Herlihy | A61B 90/11 |
| | | | | 606/130 |
| 2010/0082040 | A1 * | 4/2010 | Sahni | A61B 17/3403 |
| | | | | 606/130 |
| 2011/0009879 | A1 * | 1/2011 | Derrick | A61B 17/3403 |
| | | | | 606/130 |
| 2011/0118541 | A1 * | 5/2011 | Gassmann | 600/102 |
| 2011/0126844 | A1 * | 6/2011 | Cinquin | A61B 17/3403 |
| | | | | 128/845 |
| 2011/0190787 | A1 * | 8/2011 | Sahni | 606/130 |
| 2011/0257475 | A1 * | 10/2011 | Berkelman et al. | 600/102 |
| 2012/0022368 | A1 * | 1/2012 | Brabrand | A61B 17/3403 |
| | | | | 600/427 |
| 2013/0066232 | A1 * | 3/2013 | Schoepp | A61B 17/3403 |
| | | | | 600/567 |

FOREIGN PATENT DOCUMENTS

| | | | | |
|---|---|---|---|---|
| DE | 19902036 C1 | 3/2000 | | |
| DE | 10055293 A1 | 5/2002 | | |
| EP | 1723918 | 11/2006 | | |
| JP | 7509626 | 10/1995 | | |
| JP | 2000033070 A | 2/2000 | | |
| JP | 2004129956 | 4/2004 | | |
| JP | 2004129956 A | * | 4/2004 | A61B 1/00 |
| JP | 2006314703 A | 11/2006 | | |
| JP | 2008017903 | 1/2008 | | |
| JP | 2008173234 A | 7/2008 | | |
| JP | 2008532685 A | 8/2008 | | |
| WO | 9401149 A1 | 1/1994 | | |
| WO | 2006097925 A1 | 9/2006 | | |
| WO | 2007061386 A1 | 5/2007 | | |
| WO | 2007078003 A1 | 7/2007 | | |

* cited by examiner

SUPPORT AND GUIDE DEVICE FOR AN ENDOSCOPIC INSTRUMENT

The invention relates to a holding and guiding apparatus for an endoscopic instrument.

When using laparoscopic operating techniques, at least one endoscope having e.g., a camera is used for detection and visual control purposes and must be held and subsequently guided during intervention. The endoscope must thus be brought into different pivoted positions so that the surgeon is always provided with the desired image, the appropriate image section and the required viewing direction. The endoscope is usually operated by a medical assistant pursuant to the surgeon's instructions, wherein high levels of concentration and extremely effective communication are required for this purpose and the medical assistant must be solely concerned with this.

The need therefore exists to automate the positioning and holding of the endoscope. Solutions have already been proposed to this end, wherein the endoscope or another laparoscopic instrument is attached to a holding device disposed laterally to the operating table or disposed thereabove. Such arrangements are disadvantageous owing to their space requirement, costs, complex sterilisation procedures and the fact that the working area of the surgeon is restricted.

DE 199 02 036 C1 describes an apparatus for holding a trocar sleeve in different spatial positions. The apparatus includes a base part which can be positioned relative to the patient and has a connection member of variable stiffness. The base part surrounds a holding part for the trocar sleeve and can therefore fix the trocar sleeve in a desired orientation. Provision can be made for placement solely on the body of the patient, i.e., on the abdominal wall, only by means of the weight of the apparatus or by using a releasable adhesive.

An apparatus for positioning and holding an endoscopic instrument described in DE 100 55 293 A1 includes a holder having two bow-shaped elements which are disposed in a cross-wise manner and whose ends are each facing the surface of the body of the patient.

The bow-shaped elements can each be pivoted about an axis extending through their ends. The endoscopic instrument is disposed, guided and can possibly be fixed in an insert in the overlapping region of the two bow-shaped elements.

EP 1 723 918 A1 discloses a holding apparatus for a laparoscope, wherein provision is made for rotation along a circular horizontal guide and along a circular vertical guide. A gripping block is used to fix a trocar and is used as a guide for the laparoscope. Moreover, in the case of the known apparatus, a motorised drive can be provided for the alignment along the horizontal and vertical guides. Despite the automated rotation and fixing of the trocar with the gripping block in the horizontal and vertical circle, longitudinal displacement and/or rotation of the endoscopic instrument, located in the trocar, about its longitudinal axis must be effected manually by the surgeon who then must also hold the instrument in the respectively reached axial and rotationally-aligned position.

For Pick & Place applications, a so-called Galileo Sphere robot published e.g., in Handling/Jan. 2, 2008 under code number 219, 220, having a gripper with a mechanical wrist joint has been developed and is particularly suitable for use in large working spaces. The robot having a gripper includes a lower first curved linear drive which is provided in a plane and allows complete rotation of the gripper arm, and a second curved drive which can travel along this curved path in a plane perpendicular thereto for pivoting movement of the gripper arm. A diagonal guide provided with a carriage in the plane of the first linear drive, by means of which a gimbal for the gripper arm is produced, allows pivoting by more than 68°. Owing to direct drive technology, loads of up to 4 kg can be moved dynamically and in a highly-precise manner within an operating range of 500 mm.

The object of the invention is to provide a holding and guiding apparatus which allows in particular automated positioning and subsequent guiding of optics or of another endoscopic instrument during surgical intervention, and which is user-friendly.

This object is achieved by the invention in the case of a holding and guiding apparatus having the features of claim 1 or 2. Advantageous developments of the holding apparatus in accordance with the invention are the subject matter of the dependent Claims.

A holding and guiding apparatus in accordance with the invention thus includes a first guide device extending substantially in a plane and defining a surface, a first carriage which can travel along the first guide device, a second guide device connected to the first carriage and extending in a plane perpendicular thereto, a second carriage which can travel along the second guide device, a receiver for the endoscopic instrument, said receiver being connected to the carriage and being rotatable about its longitudinal axis and being moveable in the axial direction, drive units for the first and second carriages and for the receiver for the endoscopic instrument and a control system associated with the drive units.

The above described structure of the holding and guiding device can basically be used for applications with laparoscopic instruments, which only have to be fixed statically. Since the holding and guiding device does not need any drives if the instruments do not have to be moved, the drive units and the control system associated therewith are accordingly replaced by a holding apparatus having a releasable brake.

The holding and guiding apparatus in accordance with the invention includes an integrated arrangement of the endoscope drive by virtue of the fact that the second carriage is coupled in a movable manner with the first carriage. This allows a compact structure and thus its direct attachment to patients which means that extensive support and holding apparatuses next to or over the operating table are unnecessary. Also, the motorised drive for the required x-y-z movements or rotations and thus for the automated subsequent guiding of the endoscope is ensured. Furthermore, the movement paths can be restricted to the essential and thus the smallest possible components can be used. A larger amount of handling space is therefore available for the surgeon. The control system can be implemented for example as a voice control system or even a sensor control system. For example, a sensor system oriented towards the instrument tip can be coupled with the drive.

In a particularly expedient manner, the first guide device is formed in a circular manner. It can define a closed surface but it can also be formed as a partial ring (<360°) depending upon the circumstances of the planned intervention. The circular formation produces a particularly simple spatial movement path for the endoscope. Other configurations of the course of the first guide path (e.g., oval, elliptical) are also possible, so long as they allow control of the drive, wherein depending e.g., upon the geometry of the guide the drive paths can be calculated and thus the configuration possibilities of the guide devices are increased.

The second guide device is preferably circular, which simplifies the endoscope drive. However, as in the case of the first guide device, another curved shape or even possibly a linear shape can also be selected if this is allowed by the planned intervention, the spatial conditions and/or the drive control.

Preferably, the second guide device spans a circular arc of 90°±X°, wherein X and thus the endoscope movement paths are adapted to the selected operating technique.

In an advantageous manner, an adapter is provided for the first guide device. After applying pressure to the abdominal wall from within, this adapter is applied directly to the abdominal wall and the first guide device is then fixed thereto. The adapter can be an adhesive adapter, in particular double-sided tape. On the other hand, it is also possible to adhere the first guide device directly to the abdominal wall.

For height and/or lateral compensation, one or more adhesive adapter parts are preferably provided as an adapter. These adapter parts allow adaptation to the individual form of the abdominal wall or anatomy of the patient. Different dimensions of the adapter parts are selected corresponding thereto, and the first guide device itself-whose construction is complex in comparison therewith-does then not need to be adapted.

As an alternative to providing adhesion, provision can also be made that the adapter is a vacuum suction ring. There is then no need to provide adhesive means such as for example double-sided tape.

Preferably, the adapter is configured so as to be flexible in terms of height, which means that only one action is required to compensate for the anatomy of the patient. Simultaneously and in an expedient manner, adapter points for the first guide device are provided at spaced dispositions on the horizontal. The adapter can further contain a gel filling which is particularly capable of solidifying. In this manner, firstly the arrangement of the first guide device can be orientated in an optimum manner and can then be fixed in this position. Depending upon requirements, the solidification can be reversible or irreversible. As an alternative, other physical (e.g., magnetic) or chemical mechanisms can also be used for fixing purposes. Provision can also be made for the first guide device to be magnetically fixed to the adapter. In addition, guide bolts can be provided.

In a preferred embodiment of the invention, the first and/or second guide device is formed as a hollow body, whereby the weight of the holding and guiding apparatus is reduced and less load is applied to the abdominal wall of the patient. Suitable materials for the guide devices constructed in such a manner include for example cast aluminium or cast magnesium. Synthetic material which can be sterilised more easily can also be provided in particular as solid material, i.e., for solid constructions.

A linear motor drive, furthermore a mechanical or magnetic toothed arrangement, can be provided for the drive of the first and/or second carriage, said magnetic toothed arrangement engaging with a correspondingly magnetic pinion. Alternatively, a friction wheel drive can be provided for the first and/or second carriage. Provision of the magnetic toothed arrangement or of the friction wheel drive allows smooth guide profiles which are favourable for cleaning and ensuring sterility.

The invention will be described further hereinafter with reference to exemplified embodiments and the drawing. This presentation is used merely for illustrative purposes and is not intended to limit the invention to the specifically stated feature combinations.

Figure 2:
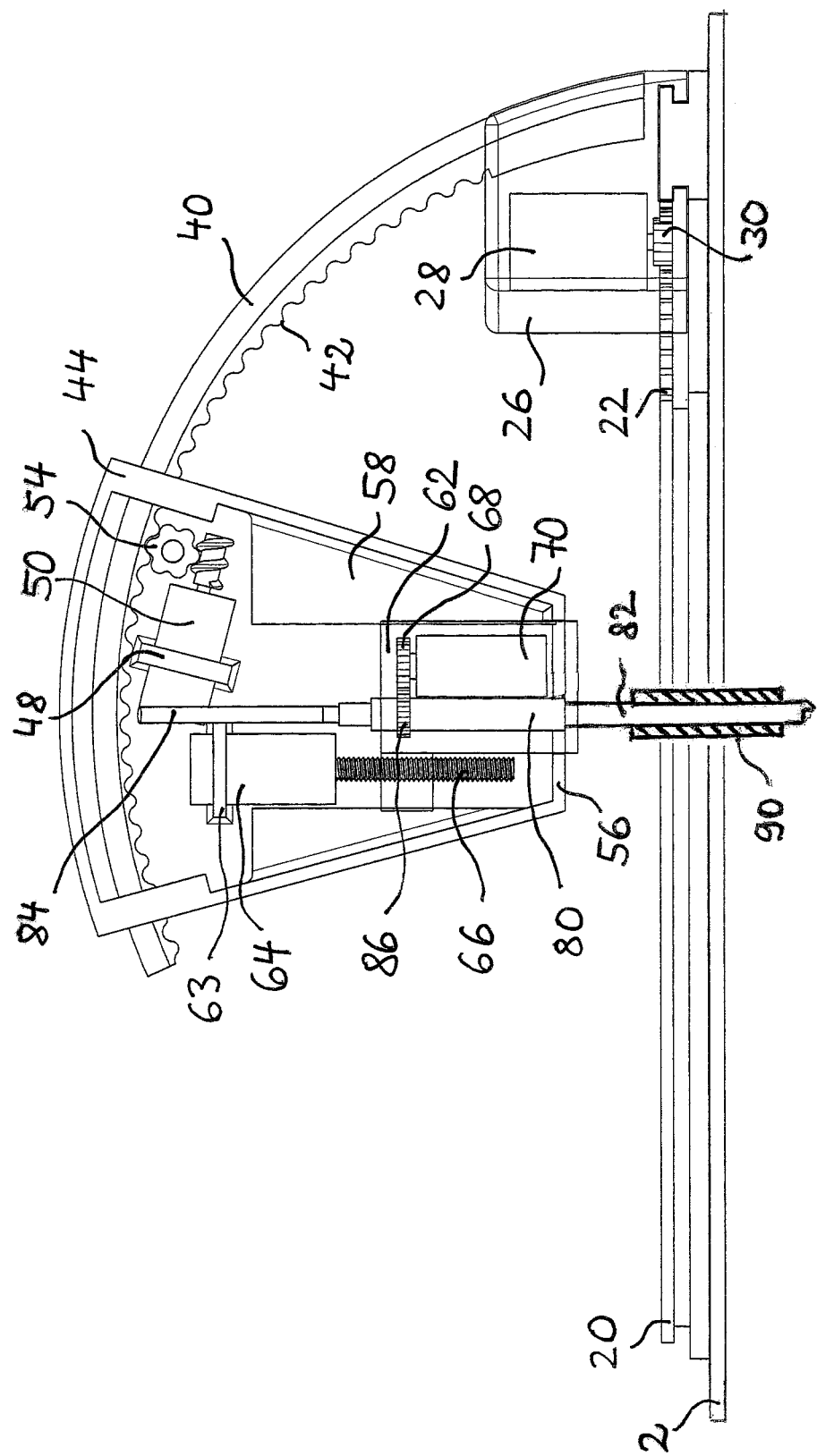
Figure 3:
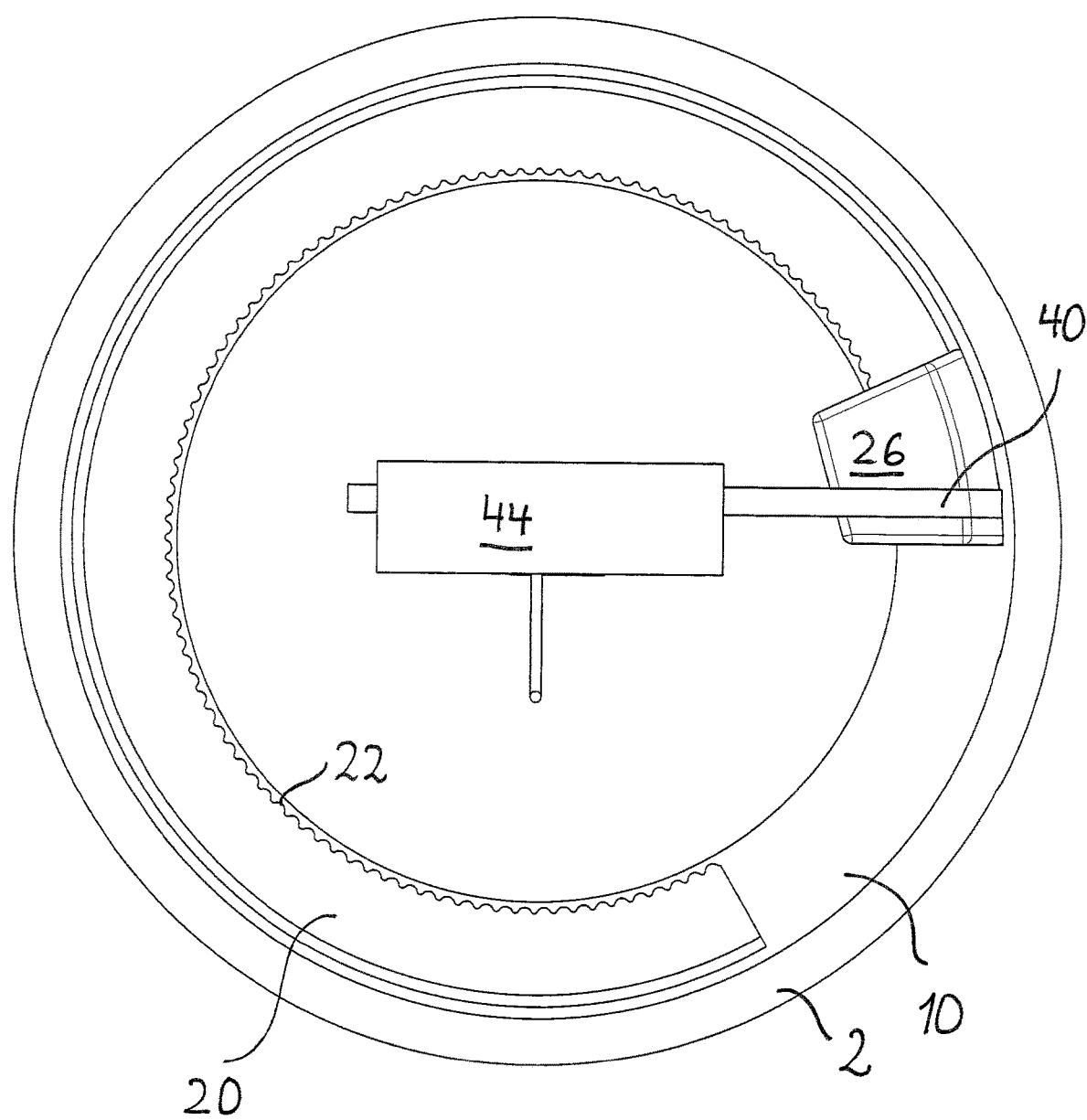

In, the drawing,

FIG. 1 shows a perspective, schematic illustration of the structure of a holding and guiding apparatus in accordance with an exemplified embodiment of the invention, FIG. 2 shows a front view of the holding and guiding apparatus of FIG. 1, and FIG. 3 shows a plan view of the holding and guiding apparatus of FIG. 1.

The holding and guiding apparatus for an endoscopic instrument shown in FIGS. 1 to 3 will be explained hereinafter. As a first guide device, the apparatus includes a guide circular ring 20, used as a base, having a horizontal toothed arrangement 22 and a guide groove 24 on the inner and outer periphery. Disposed on the guide circular ring so as to be able to travel horizontally is a first or horizontal carriage 26 having a gear motor 28 with a pinion 30. As an alternative to the toothed arrangement and the pinion, a friction wheel surface and a roller could also be provided for example, since positioning does not have to be adapted to a precisely defined degree but rather only has to be effected and followed according to the requirements of the surgeon.

The arrangement of the guide circular ring 20 on the abdominal wall 2 of a patient is only illustrated schematically. In order to fix the entire structure, an adapter is used, in this case in the form of sterile double-sided tape 10. Adapters for compensating for height differences which are provided as required for stabilising the position of the guide circular ring 20 are not illustrated.

Located on the horizontal carriage 26 as a second guide device is a vertical arcuate arm 40 having a vertical toothed arrangement 42, whose arc centre point Z is located in the centre beneath the support plane of the guide circular ring 20 of the guide circular ring 20 [sic]. Disposed on the arcuate arm 40 so as to be able to travel is a second or vertical carriage 44 having guide apertures 46. Provided for the drive of the vertical carriage 44 is a gear motor 50 attached to a holding receiver 48 and having a worm 52 and pinion 54.

As in the case of the guide circular ring 20, a friction wheel roller drive can also be provided instead of a gear toothed arrangement.

Extending through the base 56 of the vertical carriage 44 is an instrument receiver or holder 80 or guide for video optics, through which an endoscope 82 to be guided is guided and whose further connection is merely indicated at 84. A linear carriage 62 is disposed in a guided manner on an inner guide wall 58 of the vertical carriage 44 by means of guide recesses 60. The linear carriage 62 can travel up and down via a spindle gear motor 64 attached to a holding receiver 63 and via a spindle 66 in engagement therewith, in order to allow the endoscope to be moved in and out. The instrument receiver 80 is fitted with a toothed crown 86 which is engaged with a pinion 68 of a gear motor 70 for instrument rotation.

The described holding and guiding apparatus allows an endoscope 82 guided through the abdominal wall by a trocar 90 to be held and moved in a controlled or motorised manner in four degrees of freedom of movement (horizontal circle, vertical circle, axial translation and axial intrinsic rotation). The control can be effected by any command input means (keys, joystick, voice, etc.). The need to fixedly position the instrument receiver 80 in its x-y position of the skin puncture and only to pivot or rotate it vertically or horizontally in this position or to rotate it about its own axis, is met. In particular, it is also ensured that the pivot and rotation point Z is just below the abdominal wall 2 in order in this case to cause only an extremely small amount of horizontal movement against the surrounding tissue.

The invention claimed is:

1. An apparatus for holding and guiding an endoscopic instrument, comprising:
   a first guide device in a form of a circular ring extending substantially in a first plane,
   a first carriage movably connected to the first guide device,
   a second guide device extending in a second plane perpendicular to the first plane,
   wherein one end of the second guide device is connected to the first carriage, the second guide device being formed as an arc having a circle center point located in a center beneath the first plane of the first guide device,
   wherein the circle center point is the pivot and rotation point of the endoscopic instrument,
   wherein the second guide device intersects an axis of the first guide device that is perpendicular to the first plane, and is a symmetrical demarcation of the first guide device,
   a second carriage movably connected to the second guide device,
   a receiver for the endoscopic instrument, said receiver being connected to the second carriage, and being rotatable about its longitudinal axis, and being moveable in the axial direction,
   a first drive unit for the first carriage,
   a second drive unit for the second carriage,
   a third drive unit for the receiver,
   a control system associated with the first second, and third drive units, and
   an adapter associated with the first guide device.

2. The apparatus according to claim 1, wherein the first guide device is circular.

3. The apparatus according to claim 1, wherein the first guide device is formed as a partial ring.

4. The apparatus according to claim 1, wherein the second guide device extends through an arc of about 90°.

5. The apparatus according to claim 1, wherein the adapter is flexible in terms of height.

6. The apparatus according to claim 1, wherein the adapter comprises a gel filling.

7. The apparatus according to claim 6, wherein the gel filling is capable of solidifying.

8. The apparatus according to claim 1, wherein the first guide device is magnetically attached to the adapter.

9. The apparatus according to claim 1, wherein at least one of the first guide device and the second guide device is formed as a hollow body.

10. The apparatus according to claim 1, wherein a mechanical or magnetic toothed arrangement is provided for at least one of the first drive unit and the second drive unit.

11. The apparatus according to claim 1, wherein a linear motor drive is provided for at least one of the first drive unit and the second drive unit.

12. The apparatus according to claim 1, wherein the first guide device is circular and defines a closed surface.

13. The apparatus according to claim 1, wherein a friction wheel drive is provided for the second drive unit.

14. The apparatus according to claim 1, wherein a circle center point of the arc of the second guide device is a center of the first guide device.

15. The apparatus according to claim 1, wherein the axis of the first guide device that is perpendicular to the first plane is a central axis of the first guide device.

* * * * *